United States Patent
Lynn et al.

(10) Patent No.: US 9,938,361 B2
(45) Date of Patent: Apr. 10, 2018

(54) METHODS FOR PREPARING CATALYST SYSTEMS WITH INCREASED PRODUCTIVITY

(71) Applicant: Univation Technologies, LLC, Houston, TX (US)

(72) Inventors: Timothy R. Lynn, Glen Gardner, NJ (US); F. David Hussein, Cross Lanes, WV (US); R. Eric Pequeno, Baytown, TX (US); Daniel P. Zilker, Jr., Charleston, WV (US); Bruce J. Savatsky, Kingwood, TX (US); Michael D. Awe, Langhorne, PA (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 14/760,743

(22) PCT Filed: Nov. 20, 2013

(86) PCT No.: PCT/US2013/070894
§ 371 (c)(1),
(2) Date: Jul. 14, 2015

(87) PCT Pub. No.: WO2014/109832
PCT Pub. Date: Jul. 17, 2014

(65) Prior Publication Data
US 2015/0361192 A1  Dec. 17, 2015

Related U.S. Application Data

(60) Provisional application No. 61/752,182, filed on Jan. 14, 2013.

(51) Int. Cl.
| | |
|---|---|
| *C08F 4/6592* | (2006.01) |
| *C08F 10/00* | (2006.01) |
| *C08F 110/02* | (2006.01) |
| *C08F 210/16* | (2006.01) |
| *C07F 17/00* | (2006.01) |
| *C07F 7/00* | (2006.01) |
| *C08F 4/659* | (2006.01) |
| *B01J 31/22* | (2006.01) |

(52) U.S. Cl.
CPC .......... *C08F 110/02* (2013.01); *C08F 210/16* (2013.01); *B01J 31/2295* (2013.01); *B01J 2531/46* (2013.01); *B01J 2531/48* (2013.01); *B01J 2531/49* (2013.01); *C07F 7/006* (2013.01); *C07F 17/00* (2013.01); *C08F 4/65912* (2013.01); *C08F 4/65916* (2013.01); *C08F 2410/02* (2013.01)

(58) Field of Classification Search
CPC ................ C08F 4/6592; C08F 4/65912; C08F 4/65916; C08F 10/00
See application file for complete search history.

(56) References Cited

U.S. PATENT DOCUMENTS

| | | | |
|---|---|---|---|
| 5,290,745 | A | 3/1994 | Jorgensen et al. |
| 5,604,172 | A | 2/1997 | Wagner et al. |
| 5,652,314 | A | 7/1997 | Wagner Burkhard et al. |
| 6,124,229 | A | 9/2000 | Becker et al. |
| 6,605,675 | B2 | 8/2003 | Mawson et al. |
| 7,504,464 | B2 | 3/2009 | Whited et al. |
| 8,563,458 | B2 | 10/2013 | Muruganandam et al. |
| 9,133,287 | B2 | 9/2015 | Jorgensen et al. |
| 2010/0010179 | A1 | 1/2010 | Muruganandam et al. |

FOREIGN PATENT DOCUMENTS

| | | |
|---|---|---|
| EP | 0668295 | 6/1998 |
| RU | 2320673 | 3/2008 |
| WO | 0246246 | 6/2002 |
| WO | 03102037 | 12/2003 |
| WO | 2003102037 | 12/2003 |

OTHER PUBLICATIONS

International Search Report for related PCT Application PCT/US2013/070894, dated Jan. 31, 2014 (5 pgs).

*Primary Examiner* — Caixia Lu
(74) *Attorney, Agent, or Firm* — Brooks, Cameron & Huebsch, PLLC

(57) ABSTRACT

Methods for producing catalyst systems with increased productivity are disclosed. The methods may comprise providing a catalyst composition comprising a solvent and a single-site catalyst component, heating an inert gas to a temperature in a range of from about 100° C. to about 150° C., and spray drying the catalyst composition in the presence of the inert gas to form a spray-dried catalyst system. Additionally, the methods may comprise providing a catalyst composition comprising a solvent, an activator, a filler material, a metallocene catalyst, and a Group 15-containing catalyst; heating an inert gas to a temperature in a range of from about 100° C. to about 150° C.; and spray drying the catalyst composition in the presence of the inert gas to form a spray-dried catalyst system.

14 Claims, 1 Drawing Sheet

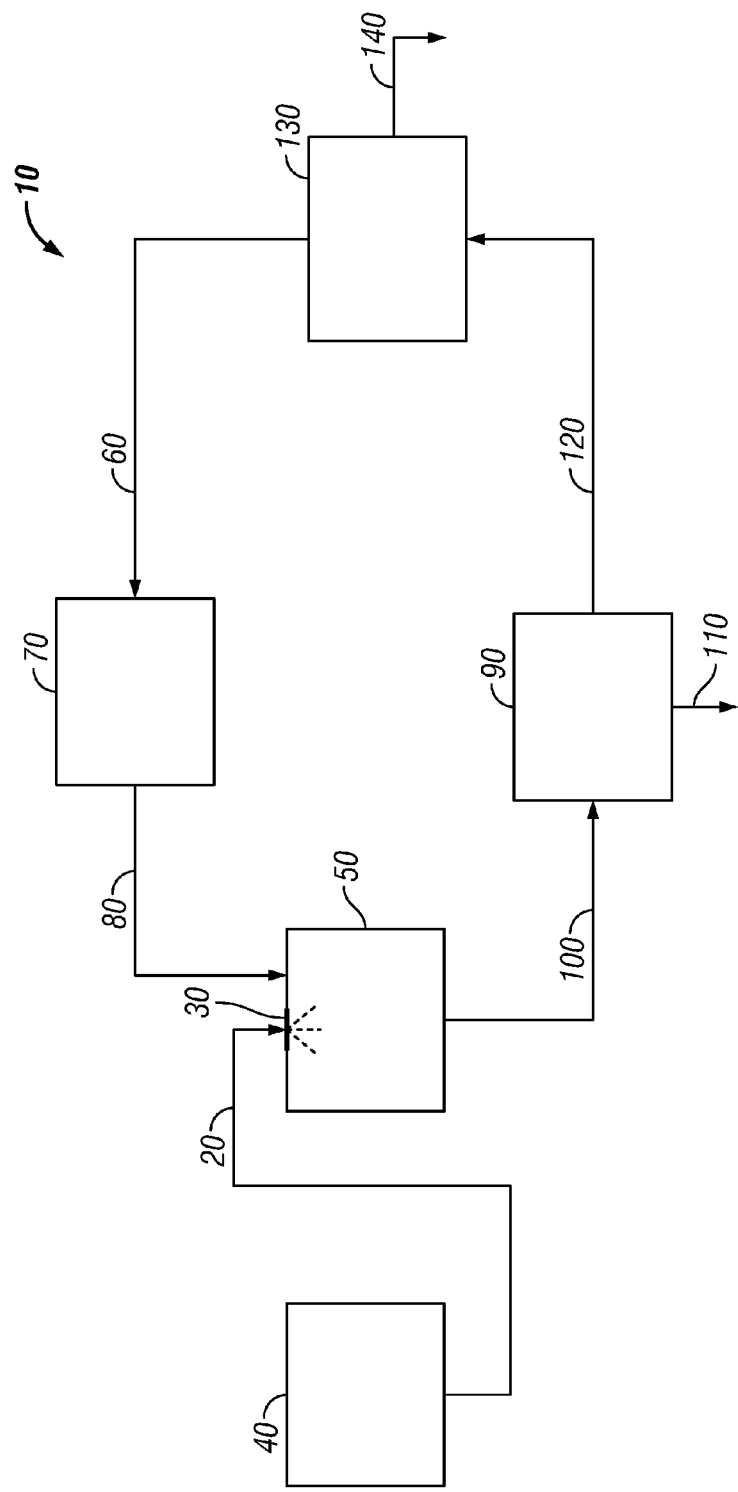

METHODS FOR PREPARING CATALYST SYSTEMS WITH INCREASED PRODUCTIVITY

This application is a National Stage Application under 35 U.S.C. § 371 of International Application Number PCT/US2013/070894, filed Nov. 20, 2013 and published as WO 2014/109832 on Jul. 17, 2014, which claims the benefit to U.S. Provisional Application 61/752,182, filed Jan. 14, 2013, the entire contents of which are incorporated herein by reference in its entirety.

FIELD

The invention generally relates to methods for preparing catalyst systems. More particularly, embodiments disclosed herein relate to methods of producing catalyst systems comprising metallocene or other single-site catalyst components, wherein the catalyst systems have increased productivity.

BACKGROUND

Advances in polymerization and catalysts have produced new polymers having improved physical and mechanical properties useful in a wide variety of products and applications. With the development of new catalysts, the choice of polymerization, such as solution, slurry, high pressure, or gas phase, for producing a particular polymer has been greatly expanded. Advances in polymerization technology have also provided more efficient, highly productive and economically enhanced processes.

Metallocene catalyst components have been widely used to produce polyolefins such as polyethylene polymers. They have provided efficient processes and a variety of new and improved polymers. In addition, catalyst systems have also been used that comprise more than one catalyst component, in effect, providing more than one active site to polymerize monomers during the polymerization process. Catalyst systems comprising two or more different catalyst components have been used, for example, to produce multimodal polymers. However, there is continued focus in the industry on developing new and improved catalyst systems. Some have focused on designing the catalyst system to produce new polymers, others on improved operability, and yet others on improving catalyst productivity. The productivity of a catalyst can be an important concern for polyolefin producers.

A number of methodologies used for delivering catalysts to reactors require the catalyst to be supported on an inert carrier such as silica. Impregnating a catalyst on a support has often been found to cause a significant decrease in catalyst activity. In addition, large particles (>25 micrometers) of the support material have frequently been found in the finished polymer product. These particles may adversely affect polymer properties. This has been observed in film applications where unexploded silica particles appear as defects or gels. Spray-drying techniques have been employed as an alternative to supported particles. Once a catalyst system has been spray dried, the spray-dried catalyst system may be added to a diluent to form a catalyst slurry and pumped to a polymerization reactor.

SUMMARY

Disclosed herein is an example method for producing a catalyst system that comprises providing a catalyst composition comprising a solvent and a single-site catalyst component, heating an inert gas to a temperature in a range of from about 100° C. to about 150° C., and spray drying the catalyst composition in the presence of the inert gas to form a spray-dried catalyst system comprising the single-site catalyst component.

Also disclosed herein is a method for producing a catalyst system that comprises providing a catalyst composition comprising a solvent, an activator, a filler material, a metallocene catalyst, and a Group 15-containing catalyst; heating an inert gas to a temperature in a range of from about 100° C. to about 150° C.; and spray drying the catalyst composition in the presence of the inert gas to form a spray-dried catalyst system comprising the activator, the filler material, the metallocene catalyst, and the Group 15-containing catalyst.

The spray-dried catalyst system may have an increase in productivity of at least about 10% in a polymerization reaction, as compared to another spray-dried catalyst system prepared from the same catalyst composition by a process that comprises heating the inert gas to a temperature of at least about 160° C.

BRIEF DESCRIPTION OF THE DRAWINGS

The drawing illustrates certain aspects of the disclosed embodiments and should not be used to limit or define the invention.

The FIGURE is a schematic block diagram representing a spray-drying apparatus suitable for forming a spray-dried catalyst system according to embodiments described herein.

DETAILED DESCRIPTION

Embodiments disclosed herein generally relate to methods for production of catalyst systems that are utilized in polyolefin polymerization systems. In particular, embodiments relate to methods of producing catalyst systems having increased productivity.

The catalyst systems are spray dried using a process that has been modified to have a lower inlet temperature for the inert drying gas. For example, the inert drying gas may be heated to a temperature in a range of from about 100° C. to about 150° C. By lowering the inlet temperature of the inert drying gas, it has been found that the productivity of the spray-dried catalyst systems may be significantly increased. Thus, these catalyst systems enable polymerization at lower reactor temperatures and thus more efficient and economical polymerization processes.

The term "catalyst," as used herein, is used interchangeably with the term "catalyst component," and includes any compound or combination of compounds and components, that is capable of increasing the rate of a chemical reaction, such as the polymerization of one or more olefins.

The term "catalyst system," as used herein, may refer to a composition comprising any number of catalysts, activators, and filler materials, and any combinations thereof, as described herein.

The terms "productivity" or "catalyst productivity," as used herein, refer to the weight of polymer produced per weight of the catalyst used in the polymerization process.

Catalyst Components

Catalyst systems produced according to disclosed embodiments may comprise a single-site catalyst component. The single-site catalyst component may include any olefin polymerization catalyst having a substantially single active site for coordination polymerization. Such catalysts are typically transition metal complexes containing a transition metal and at least one ancillary ligand that remains bonded to the transition metal during polymerization. The transition metal is generally used in a reduced cationic state and stabilized by a co-catalyst or activator. The ancillary ligands may be a structure capable of forming a bond such as, but not limited to, cyclopentadienyl or similar-type ring structures, pyridinyl, or amide ligands. For coordination polymerizations, such catalysts typically have a ligand capable of abstraction and a ligand into which the olefinic group can be inserted.

Examples of suitable single-site catalyst components include metallocene catalysts, Group-15 containing catalyst, and combinations thereof. The single-site catalyst component may be used alone or in various combinations or mixtures. The catalyst components may be used with co-catalysts, activators, and/or promoters well known in the art. For example, the single-site catalyst component may be combined with an aluminoxane as a co-catalyst (or activator) or scavenger or both. The following is a brief description of certain catalysts suitable for use in particular embodiments.

Metallocene Catalysts

The single-site catalyst component may comprise a metallocene catalyst. Suitable metallocene catalysts may be represented by Formula (I):

$$Cp^A Cp^B MX_n \qquad (I)$$

wherein M is a transition metal; each X is chemically bonded to M; each Cp group is chemically bonded to M; and n is 0 or an integer from 1 to 4. In some embodiments, n is either 1 or 2. M, X, and Cp are described in further detail below.

The metal atom "M" of the metallocene catalyst may be selected from Groups 3 through 12 atoms and lanthanide Group atoms; or may be selected from Groups 3 through 10 atoms; or may be selected from Sc, Ti, Zr, Hf, V, Nb, Ta, Mn, Re, Fe, Ru, Os, Co, Rh, Ir, and Ni; or may be selected from Groups 4, 5, and 6 atoms; or may be Ti, Zr, or Hf atoms; or may be Hf; or may be Zr. The oxidation state of the metal atom "M" can range from 0 to +7; or may be +1, +2, +3, +4, or +5; or may be +2, +3 or +4. The Cp ligand(s) form at least one chemical bond with the metal atom M. The Cp ligands are distinct from the leaving groups, X, bound to metal atom M in that they are not highly susceptible to substitution/abstraction reactions.

$Cp^A$ and $Cp^B$ are, independently, one or more rings or ring systems, at least a portion of which includes π-bonded systems, such as cycloalkadienyl ligands and heterocyclic analogues. The rings or ring systems typically comprise atoms selected from Groups 13 to 16 atoms, and, in some embodiments, the atoms that make up the $Cp^A$ and $Cp^B$ ligands are selected from carbon, nitrogen, oxygen, silicon, sulfur, phosphorous, germanium, boron, aluminum, and combinations thereof, where carbon makes up at least 50% of the ring members. In some embodiments, the $Cp^A$ and $Cp^B$ ligands are selected from substituted and unsubstituted cyclopentadienyl ligands and ligands isolobal to cyclopentadienyl. Non-limiting examples of such ligands include cyclopentadienyl, cyclopentaphenanthrenyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "$H_4$ Ind"), substituted versions thereof (as discussed and described in more detail below), and heterocyclic versions thereof.

$Cp^A$ and $Cp^B$ may be the same or different, either or both of which may contain heteroatoms and either or both of which may be substituted by any combination of one or more substitution groups, R. Non-limiting examples of substituent groups R include hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyl thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof.

More particular non-limiting examples of alkyl substituents R associated include methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins, such as, but not limited to, olefinically unsaturated substituents including vinyl-terminated ligands, for example 3-butenyl, 2-propenyl, 5-hexenyl, and the like. In some embodiments, at least two R groups, for example, two adjacent R groups, are joined to form a ring structure having from 3 to 30 atoms selected from carbon, nitrogen, oxygen, phosphorous, silicon, germanium, aluminum, boron and combinations thereof. Also, a substituent R group, such as 1-butanyl, may form a bonding association to the element M.

Each X is a leaving group bonded to the transition metal atom. For purposes herein, the term "leaving group" refers to one or more chemical moieties, such as a ligand, bound to M, that can be abstracted from the catalyst component by an activator or cocatalyst, thus producing a catalyst species active for olefin polymerization or oligomerization. Each X in is independently selected from, for example, halogen ions, hydrides, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. X may be a $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, or $C_1$ to $C_{12}$ heteroatom-containing hydrocarbons, and substituted derivatives thereof. X may be selected from hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, or $C_7$ to $C_{18}$ fluoroalkylaryls; or X may be selected from hydride, chloride, fluoride, methyl, phenyl, phenoxy, benzoxy, tosyl, fluoromethyls, and fluorophenyls; or X may be selected from $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls; or X may be selected from chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls; or X may be selected from fluoride, methyl, ethyl, propyl, phenyl, methylphenyl, dimethylphenyl, trimethylphenyl, fluoromethyls (mono-, di- and trifluoromethyls), and fluorophenyls (mono-, di-, tri-, tetra- and pentafluorophenyls).

Suitable metallocene catalysts may also be represented by Formula (II):

$$Cp^A(A)Cp^BMX_n \qquad (II)$$

These compounds are known as "bridged metallocenes." $Cp^A$, $Cp^B$, M, X and n in Formula (II) are as defined above for Formula (I). Furthermore, each Cp ligand is chemically bonded to M, and (A) is chemically bonded to each Cp.

Non-limiting examples of bridging group (A) include divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, and divalent thioethers. Additional non-limiting examples of bridging group A include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above for Formula (I) including halogen radicals and iron. More particular non-limiting examples of bridging group (A) are represented by $C_1$ to $C_6$ alkylenes, substituted $C_1$ to $C_6$ alkylenes, oxygen, sulfur, R'$_2$C=, R'$_2$Si=, —Si(R')$_2$Si(R'$_2$)—, R'$_2$Ge=, R'P= (wherein "=" represents two chemical bonds), where R' is independently selected from hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In some embodiments, the bridged metallocene catalyst component of Formula (II) has two or more bridging groups (A).

Other non-limiting examples of bridging group (A) in Formula (II) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

Bridging group (A) in Formula (II) may also be cyclic, comprising, 4 to 10 ring members or 5 to 7 ring members. The ring members may be selected from the elements mentioned above, or from one or more of B, C, Si, Ge, N and O. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination thereof.

The cyclic bridging groups (A) may be saturated or unsaturated and/or carry one or more substituents and/or be fused to one or more other ring structures. If present, the one or more substituents may be a hydrocarbyl (e.g., alkyl such as methyl) or halogen (e.g., F, Cl) or R, as defined above.

It is also contemplated that, the metallocene catalysts may include their structural or optical or enantiomeric isomers (meso and racemic isomers) and mixtures thereof. In some embodiments, the metallocene compounds may be chiral and/or a bridged metallocene catalyst compound. Further, as used herein, a single, bridged, asymmetrically substituted metallocene catalyst component having a racemic and/or meso isomer does not, itself, constitute at least two different bridged, metallocene catalyst components.

Suitable metallocene catalyst compounds and catalyst systems may be described in, for example, U.S. Pat. Nos. 4,530,914, 4,871,705, 4,937,299, 5,017,714, 5,055,438, 5,096,867, 5,120,867, 5,124,418, 5,198,401, 5,210,352, 5,229,478, 5,264,405, 5,278,264, 5,278,119, 5,304,614, 5,324,800, 5,347,025, 5,350,723, 5,384,299, 5,391,790, 5,391,789, 5,399,636, 5,408,017, 5,491,207, 5,455,366, 5,534,473, 5,539,124, 5,554,775, 5,621,126, 5,684,098, 5,693,730, 5,698,634, 5,710,297, 5,712,354, 5,714,427, 5,714,555, 5,728,641, 5,728,839, 5,753,577, 5,767,209, 5,770,753 and 5,770,664. Also, the disclosures of European publications such as EP-A-0 591 756, EP-A-0 520 732, EP-A-0 420 436, EP-B1 0 485 822, EP-B1 0 485 823, EP-A2-0 743 324 and EP-B1 0 518 092 and PCT publications WO 91/04257, WO 92/00333, WO 93/08221, WO 93/08199, WO 94/01471, WO 96/20233, WO 97/15582, WO 97/19959, WO 97/46567, WO 98/01455, WO 98/06759, and WO 98/011144 may describe useful metallocene catalysts and associated catalyst systems.

Group 15-Containing Catalysts

The single-site catalyst component may comprise a Group 15-containing catalyst. As used herein, the term "Group 15-containing catalyst" includes Group 3 to Group 12 metal complexes, wherein the metal is 2 to 8 coordinate and the coordinating moiety or moieties include at least two Group 15 atoms, and up to four Group 15 atoms. For example, the Group 15-containing catalyst may be a complex of a Group 4 metal and from one to four ligands, such that the Group 4 metal is at least 2 coordinate and the coordinating moiety or moieties include at least two nitrogens. Examples of suitable Group 15-containing catalyst are described in WO99/01460; EP0893454A1; and U.S. Pat. Nos. 5,318,935; 5,889,128; 6,333,389B2; 6,271,325B1; and 7,718,566.

In some embodiments, the Group 15-containing catalyst may include Group 4 imino-phenol complexes, Group 4 bis(amide) complexes, and Group 4 pyridyl-amide complexes that are active towards olefin polymerization to any extent. In one particular embodiment, the Group 15-containing catalyst component may include a bisamide compound such as $[2,4,6\text{-Me}_3C_6H_2)NCH_2CH_2]_2NH \text{ MBz}_2$ or $[(2,3,4,5,6\text{ Me}_5C_6)NCH_2CH_2]_2NHZrBz_2$, wherein M is a Group 4 metal, each Bz is independently a benzyl group, and Me is methyl The Group 15-containing catalyst may be described by the following formula (III):

$$\alpha_a\beta_b\gamma_g MX_n \quad\quad (III)$$

Each X of formula (III) may be independently selected from the group consisting of halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, halogenated $C_1$ to $C_{12}$ alkyls, halogenated $C_2$ to $C_{12}$ alkenyls, halogenated C6 to $C_{12}$ aryls, halogenated $C_7$ to $C_{20}$ alkylaryls, halogenated $C_1$ to $C_{12}$ alkoxys, halogenated $C_6$ to $C_{16}$ aryloxys, halogenated $C_7$ to $C_{18}$ alkylaryloxys, $C_1$ to $C_{12}$ heteroatom-containing hydrocarbons, and substituted derivatives thereof. Each X may also be selected from the group consisting of halogen substituted alkoxides, phenoxides, carboxylates, sulfonates, triflates, sulfides, and derivates thereof. Examples of suitable carboxylates include, but are not limited to, trifluoroacetate and pentafluorobenzoate. Examples of suitable sulfonates include, but are not limited to, trifluoromethanesulfonate ("triflate") and benzene sulfonate. In some embodiments, each X may also be selected from fluorinated alkyl amides, fluorinated alkenyl amides, fluorinated alkylaryl amides, fluorinated alkoxy amides, fluorinated aryloxy amides, fluorinated alkylaryloxys amides, fluorinated amides, and derivates thereof.

M of formula (III) may be selected from Group 3 to Group 12 atoms; or may be selected from Group 3 to Group 10 atoms; or may be selected from Group 3 to Group 6 atoms; or may be selected from Ni, Cr, Ti, Zr and Hf; or may be selected from Zr and Hf.

Each β and γ of formula (III) may be groups that each comprise at least one Group 14 to Group 16 atom; and β (when present) and γ are groups bonded to M through between 2 and 6 Group 14 to Group 16 atoms, at least two atoms being Group 15-containing atoms. More particularly, β and γ are groups that may be selected from Group 14 and Group 15-containing: alkyls, aryls, alkylaryls, and heterocyclic hydrocarbons, and chemically bonded combinations thereof; or may be selected from Group 14 and Group 15-containing: $C_1$ to $C_{10}$ alkyls, $C_6$ to $C_{12}$ aryls, $C_6$ to $C_{18}$ alkylaryls, and $C_4$ to $C_{12}$ heterocyclic hydrocarbons, and chemically bonded combinations thereof; or may be selected from $C_1$ to $C_{10}$ alkylamines, $C_1$ to $C_{10}$ alkoxys, $C_6$ to $C_{20}$ alkylarylamines, $C_6$ to $C_{18}$ alkylaryloxys, and $C_4$ to $C_{12}$ nitrogen-containing heterocyclic hydrocarbons, and $C_4$ to $C_{12}$ alkyl-substituted nitrogen-containing heterocyclic hydrocarbons and chemically bonded combinations thereof; or may be selected from anilinyls, pyridyls, quinolyls, pyrrolyls, pyrimidyls, purinyls, imidazyls, indolyls, $C_1$ to $C_6$ alkyl substituted groups selected from anilinyls, pyridyls, quinolyls, pyrrolyls, pyrimidyls, purinyls, imidazyls, indolyls; $C_1$ to $C_6$ alkylamine substituted groups selected from anilinyls, pyridyls, quinolyls, pyrrolyls, pyrimidyls, purinyls, imidazyls, indolyls, amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, and chemically bonded combinations thereof.

Each α of formula (III) may be a linking (or "bridging") moiety that, when present, forms a chemical bond to each of β or two γ, thus forming a "γαγ" or "γαβ" ligand bound to M; α may also comprise a Group 14 to Group 16 atom which may be bonded to M through the Group 14 to Group 16 atom; and more particularly, α may be a divalent bridging group selected from alkylenes, arylenes, alkenylenes, heterocyclic arylenes, alkylarylenes, heteroatom containing alkylenes, heteroatom containing alkenylenes, and heterocyclic hydrocarbonylenes; or α may be selected from the group consisting of $C_1$ to $C_{10}$ alkylenes, $C_2$ to $C_{10}$ alkenylenes, $C_6$ to $C_{12}$ arylenes, $C_1$ to $C_{10}$ divalent ethers, $C_6$ to $C_{12}$ O- or N-containing arylenes, $C_2$ to $C_{10}$ alkyleneamines, $C_6$ to $C_{12}$ aryleneamines, and substituted derivatives thereof.

In formula (III), a is an integer from 0 to 2, b is an integer from 0 to 2, and g is an integer from 1 to 2. In some embodiments, a may be either 0 or 1; or a may be 1. In some embodiments, a is 1, b is 0 and g is 2. In formula (IV), n is an integer from 0 to 4. In some embodiments, n may be an integer from 1 to 3; or n may be an integer from 2 to 3.

As used herein, the term "chemically bonded combinations thereof" means that adjacent groups, (β and γ groups) may form a chemical bond between them. For example, the β and γ groups may be chemically bonded through one or more α groups there between.

As used herein, the terms "alkyleneamines" and "aryleneamines" describe alkylamines and arylamines (respectively) that are deficient by two hydrogens, thus forming chemical bonds with two adjacent γ groups, or adjacent β and γ groups. Thus, an example of an alkyleneamine is —$CH_2CH_2N(CH_3)CH_2CH_2$—, and an example of a heterocyclic hydrocarbylene or aryleneamine is —$C_5H_3N$— (divalent pyridine). An "alkylene-arylamine" is a group such as, for example, —$CH_2CH_2(C_5H_3N)CH_2CH_2$—.

Activators

Catalyst systems produced according to disclosed embodiments may further comprise an activator. The activator may be spray dried with the catalyst component. As used herein, the term "activator" refers to any compound or component, or combination of compounds and components, capable of enhancing the ability of a catalyst to oligomerize or polymerize unsaturated monomers, such as olefins. It should be understood that the catalyst components may be activated for oligomerization and/or polymerization catalysis in any manner sufficient to allow coordination or cationic oligomerization and or polymerization.

Aluminoxanes activators may be utilized as an activator. Aluminoxanes may include linear, cyclic, caged, or polymeric structures. Aluminoxanes include, for example, oligomeric compounds containing —Al(R)—O— subunits, where R is an alkyl group. In some embodiments, R may be a $C_1$ to $C_8$ alkyl group. The aluminoxanes may contain linear, cyclic, caged, and/or cross-linked species. Examples of aluminoxanes include methylaluminoxane ("MAO"), modified methylaluminoxane ("MMAO"), ethylalumoxane, and isobutylalumoxane. In some embodiments, alkylaluminoxanes and modified alkylaluminoxanes are suitable as catalyst activators, particularly when the abstractable ligand is a halide. Mixtures of different aluminoxanes and modified aluminoxanes may also be used. Aluminoxanes are further described in, for example, U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1, and WO 94/10180.

In some embodiments, a visually clear methylalumoxane may be used. A cloudy or gelled aluminoxane can be filtered to produce a clear solution or clear aluminoxane can be decanted from the cloudy solution. Another aluminoxane is MMAO cocatalyst type 3A (commercially available from Akzo Chemicals, Inc. under the trade name Modified Methylalumoxane type 3A, disclosed in U.S. Pat. No. 5,041,584).

An ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (see, for example, WO 98/43983), boric acid (see, for example, U.S. Pat. No. 5,942,459) or a combination thereof, may also be used. It is also within the scope of this disclosure to use neutral or ionic activators alone or in combination with aluminoxane or modified aluminoxane activators.

Examples of neutral stoichiometric activators may include tri-substituted boron, tellurium, aluminum, gallium and indium or mixtures thereof. The three substituent groups may be each independently selected from the group of alkyls, alkenyls, halogen, substituted alkyls, aryls, arylhalides, alkoxy and halides. In embodiments, the three substituent groups may be independently selected from the group of halogen, moNo. or multicyclic (including halosubstituted) aryls, alkyls, and alkenyl compounds and mixtures thereof; in a class of embodiments are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). Alternatively, the three groups are alkyls having 1 to 4 carbon groups, phenyl, napthyl or mixtures thereof. In other embodiments, the three groups are halogenated, in an embodiment fluorinated, aryl groups. In yet other illustrative embodiments, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in, for example, European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994.

Examples of suitable activators include those described in WO 98/07515, such as tris(2,2',2"-nonafluorobiphenyl) fluoroaluminate. Combinations of activators are also contemplated, for example, aluminoxanes and ionizing activators in combination as described in EP-B1 0 573 120, WO 94/07928, WO 95/14044 and U.S. Pat. Nos. 5,153,157 and 5,453,410. WO 98/09996 describes activating metallocene catalyst compounds with perchlorates, periodates, and iodates, including their hydrates. WO 98/30602 and WO 98/30603 describe the use of lithium (2,2'-bisphenyl-ditrimethylsilicate).4THF as an activator for a metallocene catalyst compound. WO 99/18135 describes the use of organoboron-aluminum activators. EP-B1-0 781 299 describes using a silylium salt in combination with a non-coordinating compatible anion. WO 2007/024773 suggests the use of activator-supports which may comprise a chemically-treated solid oxide, clay mineral, silicate mineral, or any combination thereof. Also, methods of activation such as using radiation (see e.g., EP-B1-0 615 981), electro-chemical oxidation, and the like are also contemplated as activating methods for the purposes of rendering the neutral metallocene catalyst compound or precursor to a metallocene cation capable of polymerizing olefins. Other activators or methods for activating a metallocene catalyst compound are described in, for example, U.S. Pat. Nos. 5,849,852, 5,859,653 and 5,869,723 and PCT WO 98/32775.

Filler Materials

Catalyst systems produced according to disclosed embodiments may further comprise a filler material. In some embodiments, the filler material may be spray dried with the catalyst component and optional activator. The catalyst component and activator may, for example, be supported on the filler material in the spray-dried catalyst system, in that the catalyst component and/or activator may be deposited on, incorporated within, absorbed in or on, and/or adsorbed in or on the filler material.

Embodiments of the filler material may include any solid material which is inert to the other components of the catalyst system and during subsequent polymerization. Examples of suitable filler materials include fumed silica, non-fumed silica, boron nitride, titanium dioxide, zinc oxide, polystyrene, and calcium carbonate. Fumed hydrophobic silica may be used in particular embodiments because it may impart high viscosity to the slurry and good strength to the spray-dried catalyst system. For example, Gasil™ or Cabosil™ fumed silicas may be used. In some embodiments, the particulate material used as the filler material may have an average particle size of 50 micrometers or less or 10 micrometers or less. In particular embodiments, the filler material should be dry in that the filler material should be free of absorbed water.

Catalyst Composition

Embodiments of the present invention may include preparing a catalyst composition that is suitable for spray drying. The catalyst composition may comprise the catalyst component and optional activator in a solvent. The composition may be, for example, a solution, dispersion, or suspension of the single-site catalyst component and optionally the activator in the solvent. The composition may further comprise a filler material. In particular embodiments, a filler material such as fumed silica, for example, may be combined with a single site catalyst component and an aluminoxane to form the catalyst composition.

The combination of the solvent single-site catalyst component, activator, solvent, and/or filler material to form the catalyst composition may be performed in any order suitable for forming a catalyst composition that is suitable for spraying drying. The catalyst component and/or activator may be added to the solvent, separately or in combination, as a solution, slurry, or powder, for example. In some embodiments, the catalyst component and activator may be placed in the solvent and allowed to react, followed by addition of the filler material. Additionally, the filler material may be dispersed in the solvent, then the activator may be stirred into the solvent, and then the catalyst component may be stirred into the solvent. This catalyst composition may sit as a slurry for as long as 30 minutes or more with mild stirring or manual shaking to keep it as a suspension before spray drying.

Two or more catalyst components can be added together in the desired ratio. Additional procedures are possible, such as addition of a first catalyst component to the activator/filler material for a specified reaction time, followed by addition of a second catalyst component, mixed for another specified reaction time, after which the mixture is co-sprayed. An additive, such as 1-hexene (e.g., about 10 vol %), may be present in the activator/filler mixture prior to addition of the first catalyst component.

In some embodiments, binders may be added to the catalyst composition. For example, the binders can be added as a means of improving the particle morphology, i.e. narrowing the particle size distribution, lowering the porosity of the particles, and allowing for a reduced quantity of aluminoxane.

The catalyst composition may comprise a solvent. Examples of suitable solvents include aliphatic and aromatic hydrocarbons, such as toluene, xylene, benzene, and/or hexane. Additional solvents that are compatible with the catalyst component may be used, including fluorocarbons, for example. The solvent should generally remain liquid when the catalyst composition is prepared and be removed under the conditions employed during spray drying.

In some embodiments, the activator may be present in the catalyst composition in an amount up to about 10 weight percent ("wt %") and, in some embodiments, range from about 3 wt % to about 6 wt %. In some embodiments, the catalyst component may be present in the catalyst composition in an amount up to about 10 wt %, up to about 5 wt %, or up to about 1 wt %. In some embodiments, the filler material may be present in the catalyst composition in an amount up to about 10 weight percent ("wt %") and, in some embodiments, range from about 3 wt % to about 6 wt %. In particular embodiments, the concentration of the activator, filler material, and catalyst component in the composition may be up to about 10 wt % and, in some embodiments, range from about 5 wt % to about 10 wt %.

In some embodiments, the mole ratio of the metal in the activator to the metal in the catalyst component(s) in the catalyst composition may be in a range of about 10000:1 to about 0.5:1, about 1000:1 to about 0.5:1, about 300:1 to about 1:1, or about 150:1 to about 1:1.

In particular embodiments, the catalyst composition comprises a solvent, a filler material, an activator, and a Group 15-containing catalyst component. In some embodiments, the Group 15-containing catalyst component comprises [2,4,6-Me$_3$C$_6$H$_2$)NCH$_2$CH$_2$]$_2$NH MBz$_2$, where M is a Group 4 metal (e.g., Zr, Hf, etc.), each Bz is independently a benzyl group, and Me is methyl. In some embodiments, the Group 15-containing catalyst component comprises [2,3,4,5,6-Me$_5$C$_6$)NCH$_2$CH$_2$]$_2$NH MBz$_2$ where M is a Group 4 metal (e.g., Zr, Hf, etc.), each Bz is independently a benzyl group, and Me is methyl.

In another embodiment, the catalyst composition comprises a solvent, a filler material, an activator, and a metallocene catalyst component. In another embodiment, the catalyst composition comprises a solvent, a filler material, an activator, a Group 15-containing catalyst component, and a metallocene catalyst component.

In another embodiment, the catalyst composition comprises a solvent, a filler material, an activator, and one or more of the catalyst components described in Formulas I to III above. For example, the one or more catalyst components may comprise a metallocene catalyst represented by Formula I or II above. By way of further example, the one or more catalyst components may comprise a Group 15-containing catalyst component represented by Formula III above. By way of further example, the one or more catalyst components may comprise a metallocene catalyst represented by Formula I or II above and a Group 15-containing catalyst component represented by Formula III above In another embodiment, the catalyst composition comprises a solvent, a filler material, an activator, a Group 15-containing catalyst component and one of the following: bis(n-propyl cyclopentadienyl)-MX$_2$, (pentamethylcyclopentadienyl)(n-propylcyclopentadienyl)MX$_2$, bis(indenyl)-MX$_2$, or (tetramethylcyclopentadienyl) (n-propyl cyclopentadienyl) MX$_2$, where M is zirconium, hafnium or titanium and X is methyl, chlorine, bromine, or fluorine.

Spray-Drying Methods

Described herein are methods for spray drying the catalyst composition to form a spray-dried catalyst system. The spray-dried catalyst system may be in the form of a free-flowing powder. After spray drying, embodiments may further include combining the spray-dried catalyst system with a diluent to form a catalyst slurry suitable for use in olefin polymerization, for example. In one or more embodiments, the catalyst slurry may be combined with one or more additional catalysts or catalysts systems prior to delivery into a polymerization reactor.

Any of a variety of different spray-drying methods known in the art and suitable for forming spray-dried catalyst systems may be used according to disclosed embodiments. In some embodiments, the spray-drying method may comprise atomizing the catalyst composition. An atomizer, such as an atomizing nozzle or a centrifugal high speed disc, for example, may be used to create a spray or dispersion of droplets of the composition. The droplets of the catalyst composition may then be rapidly dried by contact with an inert drying gas. The inert drying gas may be any gas that is non-reactive under the conditions employed during atomization, such as nitrogen, for example. In some embodiments, the inert drying gas meets the catalyst composition at the atomizer, which produces a droplet stream on a continuous basis. Dried particles of the spray-dried catalyst system may be trapped out of the process in a separator, such as a cyclone, for example, which can separate solids formed from a gaseous mixture of the drying gas, solvent, and other volatile components.

In accordance with present embodiments, the inert drying gas may be heated to facilitate drying of the composition. In conventional spray-drying methods, the inert drying gas has been heated to temperatures as high as 160° C. or greater with temperatures of 170° C. being commonly used. However, embodiments disclosed herein utilize spray-drying methods that have been modified to have a lower inlet temperature for the inert drying gas. For example, the inert drying gas may have an inlet temperature in a range of from about 100° C. to about 150° C. Additionally, the inert drying gas may have an inlet temperature in a range of from about a low of 115° C., 120° C., 125° C., 130° C., 135° C., or 140° C. to a high of about 140° C., 145° C., or 150° C., where suitable temperature ranges include any lower range combined with any higher range. In particular embodiments, the inert drying gas may have an inlet temperature of about 140° C. or 145° C. In alternative embodiments, the inert drying gas may be heated to a temperature that is from about 20% to about 35% greater than the boiling point of the solvent in the composition, based on the Centigrade scale. In particular embodiments, the inert drying gas may be heated to a temperature that is from about 25% to about 27% greater than the boiling point of the solvent, based on the Centigrade scale.

By adjusting the size of the orifices of the atomizing nozzle employed during spray drying, for example, it may be possible to obtain particles of the catalyst system having the desired particle size. Alternatively, for other types of atomizers such as discs, rotational speed, disc size, and number/size of holes may be adjusted to control particle size. In some embodiments, the spray-dried catalyst system may have an average particle size in a range of from about 5 micrometers to about 200 micrometers and, alternatively from about 10 micrometers to about 30 micrometers.

In some embodiments, the spray-dried catalyst system may comprise the filler material in an amount up to about 90 wt %. For example, the filler material may be present in an amount in a range of from about 1 wt % to about 70 wt %. In particular embodiments, the filler material may be present in an amount of about 40 wt % to about 65 wt %.

In some embodiments, the mole ratio of the metal in the activator to the metal in the catalyst component(s) in the spray-dried catalyst system may be in a range of about 10000:1 to about 0.5:1, about 1000:1 to about 0.5:1, about 300:1 to about 1:1, or about 150:1 to about 1:1.

In some embodiments, the spray-dried catalyst system may comprise the catalyst component in an amount up to about 10 wt %. For example, the catalyst may be present in an amount in a range of from about 1 wt % to about 10 wt %. In particular embodiments, the catalyst may be present in an amount of about 1 wt % to about 6 wt %.

In some embodiments, the spray-dried catalyst system may comprise the activator in an amount up to about 60 wt %. For example, the activator may be present in an amount in a range of from about 10 wt % to about 60 wt %. In particular embodiments, the activator material may be present in an amount of about 30 wt % to about 60 wt %.

By spray drying the catalyst composition at lower inlet temperature for the inert drying gas, embodiments may provide a catalyst system which demonstrates increased productivity when used in a polymerization process. For example, the productivity of the catalyst system may be increased by up to 40% or more in a polymerization reaction, as compared to the catalyst system produced by spray drying of the same catalyst composition at a temperature of about 160° C. or greater. In some embodiments, the productivity may be increased by at least about 10%, at least about 20%, at least about 30%, or at least about 40%. In some embodiments, the catalyst system may have a productivity greater than 4,500 grams of polymer per gram of catalyst system ("g/g"), greater than about 5,000 g/g, greater than about 6,000 g/g, or greater than about 7,000 g/g.

The FIGURE is a schematic diagram illustrating an example process 10 that can be used for spray drying of the catalyst composition in accordance with disclosed embodiments. As illustrated, stream 20 of the catalyst composition may be delivered to atomizer 30, which may be an atomizing disc or nozzle, for example, by way of feed tank 40. Droplets of the catalyst composition are formed as the catalyst composition exits the atomizer 30 into the drying chamber 50. In the drying chamber 50, the droplets of the catalyst composition may be dried in the presence of a heated inert gas. As illustrated, a gas stream 60 comprising an inert gas may be heated in heater 70. The heater 70 may heat the gas stream 60 to a temperature in a range of from about 100° C. to about 150° C., for example. A heated gas stream 80 may exit the heater 70 and be fed to the drying chamber 50.

Dried particles of the catalyst system may form in the drying chamber 50, for example, as the solvent and other volatile components may be removed from the droplets. The spray-dried catalyst system formed in the drying chamber 50 may be carried by the inert gas into separator 90 via stream 100, where the spray-dried catalyst system may be separated from the inert gas and removed from the separator 90 via catalyst stream 110. In some embodiments, the separator 90 may be a cyclone separator. In the illustrated embodiment, a gas stream 120 comprising the inert gas may be withdrawn from the separator 90. The gas stream 120 may further comprise the solvent that was removed from the catalyst composition as well as other volatile components, if any, that may have been present in the catalyst composition. A condenser 130 may be used to separate the solvent and other volatile components from the inert gas in the gas stream 120. Stream 60 comprising the inert gas may be removed from the condenser 130 and recycled for production of additional spray-dried catalyst. A condensed solvent stream 140 may also be withdrawn from the condenser 130.

Continuity Additives

In the polymerization processes disclosed herein, it may be desired to use a continuity additive, for example, to control or potentially even eliminate reactor discontinuity events, which in general are a disruption in the continuous operation of a polymerization reactor. As used herein, the term "continuity additive or aid" and "antifoulant agent" refer to compounds or mixtures of compounds, such as solids or liquids, that are useful in gas phase or slurry phase polymerization processes to reduce or eliminate fouling of the reactor, where "fouling" may be manifested by any number of phenomena including sheeting of the reactor walls, plugging of inlet and outlet lines, formation of large agglomerates, or other forms of reactor upsets known in the art. For purposes here, the terms may be used interchangeably. In accordance with embodiments, the continuity additive may be used as a part of the catalyst composition or introduced directly into the reactor independently of the catalyst composition. In a class of embodiments, the continuity additive is supported on the inorganic oxide of the supported catalyst composition described herein.

The specific continuity additive used may depend at least in part upon the nature of the static charge, the particular polymer being produced, and/or the particular catalyst being used. Non-limiting examples of continuity additives comprise fatty acid amines, amide-hydrocarbon or ethoxylated-amide compounds such as described as "surface modifiers" in WO 96/11961; carboxylate compounds such as aryl-carboxylates and long chain hydrocarbon carboxylates, and fatty acid-metal complexes; alcohols, ethers, sulfate compounds, metal oxides and other compounds known in the art. Some specific examples of continuity additives include 1,2-diether organic compounds, magnesium oxide, ARMOSTAT 310, ATMER 163, ATMER AS-990, and other glycerol esters, IRGASTAT AS-990 and other ethoxylated amines (e.g., N,N-bis(2-hydroxyethyl)octadecylamine), alkyl sulfonates, and alkoxylated fatty acid esters; STADIS 450 and 425, KEROSTAT CE 4009 and KEROSTAT CE 5009, chromium N-oleylanthranilate salts, calcium salts of a Medialan acid and di-tert-butylphenol; POLYFLO 130, TOLAD 511 (a-olefin-acrylonitrile copolymer and polymeric polyamine), EDENOL D32, aluminum stearate, aluminum distearate, sorbitan-monooleate, glycerol monostearate, methyl toluate, dimethyl maleate, dimethyl furnarate, triethylamine, 3,3-diphenyl-3-(imidazol-1-yl)-propin, and like compounds. In some embodiments, the continuity additive is a metal carboxylate salt as described, optionally, with other compounds as described in this section.

Still other continuity additives can comprise polyethylenimines having the structure —$(CH_2—CH_2—NH)_n$—, where n can be from 10 to 10,000. The polyethyleneimines may be linear, branched, or hyperbranched (i.e., forming dendritic or arborescent polymer structures). They can be a homopolymer or copolymer of ethyleneimine or mixtures thereof (referred to as polyethyleneimine(s) hereafter). Although linear polymers represented by the chemical formula —$[CH_2\ CH_2\ NH]$— may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Yet additional continuity additives can comprise a polyetheramine. As used herein, the term "polyetheramine" refers to a polymer containing a polyether backbone that terminates in at least one amino group. The polyether backbone may be, for example, ethylene oxide-based, propylene oxide-based, 1,2 butylene oxide-based, tetramethylene oxide-based, or any combination thereof. The polyetheramines may be, for example, a block copolymer, a graft copolymer, or a block-graft copolymer. In an embodiment, the polyetheramine is a diblock copolymer or a triblock copolymer. In an embodiment, the polyetheramine may be a block copolymer of ethylene oxide and propylene oxide. Suitable polyetheramines comprise, for example, monoamines, diamines, and triamines. In an embodiment, the polyether backbone terminates in at least one primary amino group. In another embodiment, the polyether backbone terminates in at least one secondary amino group. In yet another embodiment, the polyether backbone terminates in at least one tertiary amino group. Suitable polyetheramines include those commercially available from Huntsman Corporation under the trade name JEFFAMINE® polyetheramines Examples of commercially available polyetheramines for use in embodiments of the present invention include, but are not limited to: JEFFAMINE® ED series polyetheramines, such as JEFFAMINE® HK-511 polyetheramine, JEFFAMINE® ED-600 polyetheramine, JEFFAMINE® ED-900 polyetheramine, and JEFFAMINE® ED-2003 polyetheramine; JEFFAMINE® M series polyetheramines, such as JEFFAMINE® M-600 polyetheramine, JEFFAMINE® M-1000, JEFFAMINE® M-2005 polyetheramine, and JEFFAMINE® M-2070 polyetheramine; and JEFFAMINE® D series polyetheramines, such as JEFFAMINE® D-230 polyetheramine, JEFFAMINE® D-400, JEFFAMINE® D-2000 polyetheramine, and JEFFAMINE® D-4000 polyetheramine.

Any of the aforementioned continuity additives may be employed either alone or in combination as a continuity additive. For example, the metal carboxylate salt may be combined with an amine containing control agent (e.g., an extracted carboxylate metal salt with any family member belonging to the KEMAMINE (available from Crompton Corporation) or ATMER (available from ICI Americas Inc.) family of products).

Other continuity additives useful in embodiments disclosed herein are well known to those in the art. Regardless of which continuity additives are used, care should be exercised in selecting an appropriate continuity additive to avoid introduction of poisons into the reactor. In addition, in selected embodiments, the smallest amount of the continuity additives necessary to bring the static charge into alignment with the desired range should be used.

The continuity additive can be introduced to the reactor as a combination of two or more of the above listed continuity additives. The continuity additive(s) can be introduced to the reactor in the form of a solution or slurry. The continuity additive can be introduced to the reactor as an individual feed or can be combined with other feeds prior to introduction to the reactor. For example, the continuity additive can be combined with the catalyst or catalyst slurry prior to introducing the combined catalyst slurry/continuity additive mixture to the reactor.

The amount of continuity additive introduced to the reactor and/or the catalyst slurry can be sufficient to provide a continuity additive concentration of from about 0.05 ppmw to about 200 ppmw, based on the polymer production rate. For example, the continuity additive can be introduced to the reactor, i.e. directly to the reactor and/or combined with the catalyst slurry, in an amount ranging from a low of about 1 ppmw, about 2 ppmw, or about 3 ppmw to a high of about 35 ppmw, about 45 ppmw, or about 55 ppmw, based on the polymer production rate. The amount of continuity additive introduced to the reactor can depend, at least in part, on the particular catalyst composition, reactor pre-conditioning such as coatings to control static buildup, and/or other factors.

Polymerization Processes

Embodiments for producing polyolefins disclosed herein may employ any suitable process for the polymerization of olefins, including any suspension, solution, slurry, or gas phase process, using known equipment and reaction conditions, and are not limited to any specific type of polymerization system.

In general, the polymerization process may be a continuous gas phase process, such as a fluid bed process. In an embodiment, a fluid bed reactor may have a reaction zone and a velocity reduction zone (i.e., disengagement zone). The reaction zone includes a bed of growing polymer particles, formed polymer particles and a minor amount of catalyst particles fluidized by the continuous flow of the gaseous monomer and diluent to remove heat of polymerization through the reaction zone. Optionally, some of the recirculated gases may be cooled and compressed to form liquids that increase the heat removal capacity of the circulating gas stream when readmitted to the reaction zone. A suitable rate of gas flow may be readily determined by simple experiment. Makeup of gaseous monomer to the circulating gas stream is at a rate equal to the rate at which particulate polymer product and monomer associated therewith is withdrawn from the reactor, and the composition of the gas passing through the reactor is adjusted to maintain an essentially steady state gaseous composition within the reaction zone. The gas leaving the reaction zone is passed to the velocity reduction zone where entrained particles are removed. Finer entrained particles and dust may be removed in a cyclone and/or fine filter. The gas is passed through a heat exchanger wherein the heat of polymerization is removed, compressed in a compressor and then returned to the reaction zone.

Useful gas phase polymerization processes include those that utilize a fluidized bed reactor. This type reactor, and means for operating the reactor, are well known and are described in, for example, U.S. Pat. Nos. 3,709,853; 4,003, 712; 4,011,382; 4,302,566; 4,543,399; 4,882,400; 5,352, 749; 5,541,270; EP-A-0 802 202. These patents disclose gas phase polymerization processes wherein the polymerization medium is either mechanically agitated or fluidized by the continuous flow of the gaseous monomer and diluent.

The process described herein is suitable for the production of homopolymers of olefins, including ethylene, and/or copolymers, terpolymers, and the like, of olefins, including polymers comprising ethylene and at least one or more other olefins. The olefins may be alpha-olefins. The olefins, for example, may contain from 2 to 16 carbon atoms in one embodiment. In other embodiments, ethylene and a comonomer comprising from 3 to 12 carbon atoms, or from 4 to 10 carbon atoms, or from 4 to 8 carbon atoms, may be used. In an embodiment, the olefin is a monomer selected from the group consisting of ethylene, propylene, and any combination thereof.

In embodiments, polyethylene may be prepared by the process disclosed herein. Such polyethylene may include homopolymers of ethylene and interpolymers of ethylene and at least one alpha-olefin wherein the ethylene content is at least about 50% by weight of the total monomers involved. Olefins that may be used herein include ethylene, propylene, 1-butene, 1-pentene, 1-hexene, 1-heptene, 1-octene, 4-methylpent-1-ene, 1-decene, 1-dodecene, 1-hexadecene and the like. Also usable are polyenes such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene, and olefins formed in situ in the polymerization medium. When olefins are formed in situ in the polymerization medium, the formation of polyolefins containing long chain branching may occur.

The content of the alpha-olefin incorporated into the copolymer may be no greater than 30 mol % in total, or may be from 3 to 20 mol %. The term "polyethylene" when used herein is used generically to refer to any or all of the polymers comprising ethylene described above.

In other embodiments, propylene-based polymers may be prepared by processes disclosed herein. Such propylene-based polymers may include homopolymers of propylene and interpolymers of propylene and at least one alpha-olefin wherein the propylene content is at least about 50% by weight of the total monomers involved. Comonomers that may be used may include ethylene, 1-butene, 1-pentene, 1-hexene, 1-heptene, 1-octene, 4-methylpentene-1,1-decene, 1-dodecene, 1-hexadecene and the like. Also usable are polyenes such as 1,3-hexadiene, 1,4-hexadiene, cyclopentadiene, dicyclopentadiene, 4-vinylcyclohexene-1,1,5-cyclooctadiene, 5-vinylidene-2-norbornene and 5-vinyl-2-norbornene, and olefins formed in situ in the polymerization medium. When olefins are formed in situ in the polymerization medium, the formation of polyolefins containing long chain branching may occur. In one embodiment, the content of the alpha-olefin comonomer incorporated into a propylene-based polymer may be no greater than 49 mol % in total, from 3 to 35 mol % in other embodiments.

Hydrogen gas is often used in olefin polymerization to control the final properties of the polyolefin. Increasing the concentration (partial pressure) of hydrogen may increase the melt flow index (MFI) and/or melt index (MI) of the polyolefin generated. The MFI or MI can thus be influenced by the hydrogen concentration. The amount of hydrogen in the polymerization may be expressed as a mole ratio relative to the total polymerizable monomer, for example, ethylene, or a blend of ethylene and hexene or propylene. In an embodiment, the amount of hydrogen used in the polymerization processes is an amount sufficient to achieve the desired MFI or MI of the final polyolefin resin. Melt flow rate for polypropylene may be measured according to ASTM D 1238 (230° C. with 2.16 kg weight); melt index ($I_2$) for polyethylene may be measured according to ASTM D 1238 (190° C. with 2.16 kg weight).

Other gas phase processes contemplated include series or multistage polymerization processes. For example, a staged reactor employing two or more reactors in series may be used, wherein one reactor may produce, for example, a high molecular weight component and another reactor may produce a low molecular weight component. In some embodiments, the polyolefin is produced using a staged gas phase reactor. Such polymerization systems are described in, for example, U.S. Pat. Nos. 5,627,242; 5,665,818; and 5,677, 375; and European publications EP-A-0 794 200; EP-B1-0 649 992, EP-A-0 802 202 and EP-B-634 421.

In one embodiment, the one or more reactors in a gas phase or fluidized bed polymerization process may have a pressure ranging from about 0.7 to about 70 bar (about 10 to about 1,000 psia), or from about 14 to about 42 bar (about 200 to about 600 psia). In one embodiment, the one or more reactors may have a temperature ranging from about 10° C. to about 150° C., or from about 40° C. to about 125° C. In an embodiment, the reactor temperature may be operated at the highest feasible temperature taking into account the sintering temperature of the polymer within the reactor. In embodiments, the superficial gas velocity in the one or more reactors may range from about 0.2 to about 1.1 meters/ second (about 0.7 to about 3.5 feet/second), or from about 0.3 to about 0.8 meters/second (about 1.0 to about 2.7 feet/second).

Some embodiments may be used with gas phase polymerization systems, at superatmospheric pressures in the range from 0.07 to 68.9 bar (1 to 1,000 psig), from 3.45 to 27.6 bar (50 to 400 psig) in some embodiments, from 6.89 to 24.1 bar (100 to 350 psig) in other embodiments, and temperatures in the range from 30 to 130° C., or from 65 to 110° C., from 75 to 120° C. in other embodiments, or from 80 to 120° C. in further embodiments. In some embodiments, operating temperatures may be less than 112° C. In embodiments, stirred or fluidized bed gas phase polymerization systems may be used.

The polymerization process may be a continuous gas phase process that includes the steps of: (a) introducing a recycle stream (including ethylene and alpha olefin monomers) into the reactor; (b) introducing the supported catalyst composition; (c) withdrawing the recycle stream from the reactor; (d) cooling the recycle stream; (e) introducing into the reactor additional monomer(s) to replace the monomer(s) polymerized; (f) reintroducing the recycle stream or a portion thereof into the reactor; and (g) withdrawing a polymer product from the reactor.

In embodiments, one or more olefins, $C_2$ to $C_{30}$ olefins or alpha-olefins, including ethylene or propylene or combinations thereof, may be prepolymerized in the presence of a metallocene catalyst composition prior to the main polymerization. The prepolymerization may be carried out batchwise or continuously in gas, solution or slurry phase, including at elevated pressures. The prepolymerization may take place with any olefin monomer or combination and/or in the presence of any molecular weight controlling agent such as hydrogen. For examples of prepolymerization procedures, see U.S. Pat. Nos. 4,748,221; 4,789,359; 4,923,833; 4,921, 825; 5,283,278; and 5,705,578 and European publication EP-B-0279 863 and WO 97/44371.

Processes disclosed herein may optionally use inert particulate materials as fluidization aids. These inert particulate materials can include carbon black, silica, talc, and clays, as well as inert polymeric materials. Carbon black, for example, has a primary particle size of about 10 to about 100 nanometers, an average size of aggregate of about 0.1 to about 30 microns, and a specific surface area from about 30 to about 1500 m$^2$/g. Silica has a primary particle size of about 5 to about 50 nanometers, an average size of aggregate of about 0.1 to about 30 microns, and a specific surface area from about 50 to about 500 m$^2$/g. Clay, talc, and polymeric materials have an average particle size of about 0.01 to about 10 microns and a specific surface area of about 3 to 30 m$^2$/g. These inert particulate materials may be used in amounts ranging from about 0.3 to about 80%, or from about 5 to about 50%, based on the weight of the final product. They are especially useful for the polymerization of sticky polymers as disclosed in U.S. Pat. Nos. 4,994,534 and 5,304,588.

Chain transfer agents, promoters, scavenging agents and other additives may be, and often are, used in the polymerization processes disclosed herein. Chain transfer agents are often used to control polymer molecular weight. Examples of these compounds are hydrogen and metal alkyls of the general formula M$^x$R$_y$, where M is a Group 3-12 metal, x is the oxidation state of the metal, typically 1, 2, 3, 4, 5 or 6, each R is independently an alkyl or aryl, and y is 0, 1, 2, 3, 4, 5, or 6. In some embodiments, a zinc alkyl is used, such as diethyl zinc. Typical promoters may include halogenated hydrocarbons such as CHCl$_3$, CFCl$_3$, CH$_3$—CCl$_3$, CF$_2$Cl—CCl$_3$, and ethyltrichloroacetate. Such promoters are described in, for example, U.S. Pat. No. 4,988,783. Other organometallic compounds such as scavenging agents for poisons may also be used to increase catalyst activity. Examples of these compounds include metal alkyls, such as aluminum alkyls, for example, triisobutylaluminum. Some compounds may be used to neutralize static in the fluidized-bed reactor, others known as drivers rather than antistatic agents, may consistently force the static from positive to negative or from negative to positive. The use of these additives is well within the skill of those skilled in the art. These additives may be added to the circulation loops, riser, and/or downer separately or independently from the catalyst, or as part of the catalyst In embodiments, the reactors disclosed herein are capable of producing greater than 500 lbs of polymer per hour (227 kg/hr) to about 300,000 lbs/hr (136,000 kg/hr) or higher of polymer, preferably greater than 1000 lbs/hr (455 kg/hr), more preferably greater than 10,000 lbs/hr (4540 kg/hr), even more preferably greater than 25,000 lbs/hr (11,300 kg/hr), still more preferably greater than 35,000 lbs/hr (15,900 kg/hr), still even more preferably greater than 50,000 lbs/hr (22,700 kg/hr) and most preferably greater than 65,000 lbs/hr (29,000 kg/hr) to greater than 150,000 lbs/hr (68,100 kg/hr).

In accordance with disclosed embodiments, the catalyst systems may be spray dried using a process that has been modified to have a lower inlet temperature for the inert drying gas. For example, the inert drying gas may be heated to a temperature in a range of from about 130° C. to about 150° C. By lowering the inlet temperature of the inert drying gas, it has been found that the productivity of the spray-dried catalyst systems may be significantly The polymers produced by embodiments of the process of the invention can be used in a wide variety of products and end-use applications. The polymers produced by the process of the invention may include, but are not limited to, linear low density polyethylene, low density polyethylenes, and high density polyethylenes.

The polymers, including ethylene and propylene based polymers, have a density, for example, in the range of from about 0.86 g/cm$^3$ to about 0.97 g/cm$^3$. In other embodiments, the polymers have a density in the range of from about 0.88 g/cm$^3$ to about 0.965 g/cm$^3$ or in the range of from about 0.900 g/cm$^3$ to about 0.96 g/cm$^3$.

The polymers produced by the process of the invention may have a molecular weight distribution, a weight average molecular weight to number average molecular weight (Mw/Mn), for example, of greater than 1.5 to about 15. In other embodiments, the polymers may have an Mw/Mn of greater than 2 to about 10 or greater than about 2.2 to less than about 8.

The polymers of the present invention may have a melt index (MI) or (I2) as measured by ASTM-D-1238-E (190° C./2.16 kg), for example, in the range from 0.01 dg/min to 1000 dg/min. In other embodiments, the polymers may have a melt index of from about 0.01 dg/min to about 100 dg/min or from about 0.1 dg/min to about 100 dg/min.

The polymers of the invention in an embodiment may have a melt index ratio (I21/I2) (I21 is measured by ASTM-D-1238-F, [190° C./21.6 kg]), for example, of from 5 to 300. In other embodiments, the polymers may have a melt index ration of from about 10 to less than 250, from 15 to 200, or from 20 to 180.

The polymers of the invention may be blended and/or coextruded with any other polymer. Non-limiting examples of other polymers include linear low density polyethylenes produced via conventional and/or single-site catalysis, elastomers, plastomers, high pressure low density polyethylene, high density polyethylenes, polypropylenes and the like.

Polymers produced by the process of the invention and blends thereof are useful in such forming operations as film, pipe, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers may include, are not limited to, melt spinning, solution spinning and melt blown fiber operations for use in woven or non-woven form to make filters, diaper fabrics, medical garments, geotextiles, etc. Extruded articles may include medical tubing, wire and cable coatings, geomembranes, and pond liners. Molded articles include single and multi-layered constructions in the form of bottles, tanks, large hollow articles, rigid food containers and toys, etc.

EXAMPLES

The following examples are put forth so as to provide those skilled in the art with a complete disclosure and description of how to make and use the methods and systems of the invention, and are not intended to limit the scope of that which the inventors regard as their invention.

Example 1

A high-temperature spray-drying process was used to produce a first spray-dried catalyst system (comparative), referred to herein as Catalyst A. An example of a typical procedure used is as follows: a suspension was prepared by combining 1040 lbs of toluene, 804 lbs of 10 wt % methylalumoxane in toluene, supplied by Albemarle, and 110 lbs of Cabosil TS-610 fumed silica, supplied by Cabot, and letting this mixture agitate for 1 hour at 30° C. 4.89 lbs of bis(2-(pentamethylphenylamido)ethyl)amine zirconium dibenzyl, supplied by Koei Chemical Company, LTD., and 0.95 lbs of (tetramethylcyclopentadiene)(n-propylcyclopentadiene) zirconium dichloride, supplied by Boulder Scientific Company, were added to the toluene/MAO/fumed silica suspension and mixed for 1 hour at 30° C. This suspension is now ready for spray drying. The suspension was fed to the spray dryer at a feed rate of 180 pounds per hour. The rotary disc atomizer speed was maintained at 21,600 rpm. The dryer had an inlet nitrogen gas temperature of 172° C. with a gas flow rate of 780 pounds per hour. The outlet temperature of the drying chamber was 80° C. The powder produced by the spray-drying process was separated from the gas stream by a cyclone, and the powder dropped into an agitated vessel containing 493 lbs of Hydrobrite 380 PO white mineral oil, supplied by Sonneborne, and 52 lbs of Isopar C, an aliphatic hydrocarbon mixture supplied by ExxonMobil. The vessel was maintained at 30° C. After all of the feedstock suspension had been spray dried, an additional 33 lbs of mineral oil and 27 lbs of Isopar C were added to wash down the upper walls of the vessel. The mineral oil suspension agitated ~12 hours and was discharged into a product cylinder.

A low-temperature spray-drying process was used to produce a second spray-dried catalyst system, referred to herein as Catalyst B. The toluene suspension was prepared using the identical charge weights and preparation conditions as used for Catalyst A. The resultant slurry was then sprayed dried in a pilot-scale dryer. The slurry was fed to the spray dryer at a feed rate of 112 pounds per hour. The rotary disc atomizer speed was maintained at 21,600 rpm. The dryer had an inlet nitrogen gas temperature of 140° C. with a gas flow rate of 760 pounds per hour. The outlet temperature of the drying chamber was 80° C. As with Catalyst A, the powder produced in the spray dryer was separated from the drying gas in a cyclone, with the powder dropping from the cyclone into an agitated vessel containing the same weights of Hydrobrite 380 PO white mineral oil and Isopar C. The same amounts of wash liquids were used and the suspension mixed for ~12 hours before being discharged into a product cylinder.

Both Catalyst A and Catalyst B have nominal compositions of 17.3 wt % Al, 0.49 wt % Zr, 3 wt % Zr, and a D50 particle size of 19 microns. The concentration of the catalyst powder in the mineral oil suspension is 23 w %.

Table 1 below provides a comparison of example conditions used in production of Catalyst A using the high-temperature spray-drying process and Catalyst B using the low-temperature spray-drying process.

TABLE 1

| Process Parameter | High-Temperature Spray-Drying Process (comparative) | Low-Temperature Spray-Drying Process |
|---|---|---|
| Inlet Gas Temperature, ° C. | 172 | 140 |
| Outlet Gas Temperature, ° C. | 80 | 80 |
| Gas Flow Rate, lb/hr | 780 | 760 |
| Feedstock Flow Rate, lb/hr | 180 | 112 |

As illustrated by Table 1, the low-temperature drying process used an inlet gas temperature of 140° C. as compared to an inlet gas temperature of 172° C. for the high-temperature spray-drying process. The differences in feedstock flow rate is a result of the lower drying temperature for the inlet gas temperature. As less heat is entering the drying chamber, the feedstock flow rate has been reduced to maintain the target outlet gas temperature of 80° C.

Example 2

The spray-dried catalyst systems described above were used in ethylene polymerizations conducting in a fluidized-bed gas-phase polymerization reactor on a pilot scale. The fluidized bed was made up of polymer granules. The reactor was operated to produce a pipe product of about 7 I21 flow index and 0.949 g/cm$^3$ density. The gaseous feed streams of ethylene and hydrogen together with liquid comonomer were introduced below the reactor bed into the recycle gas line. Hexene was used as comonomer. The individual flow rates of ethylene, hydrogen and comonomer were controlled to maintain fixed composition targets. The ethylene concentration was controlled to maintain a constant ethylene partial pressure. The hydrogen concentration was controlled to maintain a constant hydrogen to ethylene mole ratio. The concentrations of all the gases were measured by an on-line gas chromatograph to ensure relatively constant composition in the recycle gas stream.

The spray-dried catalyst system was injected directly into the reactor as a slurry in purified mineral oil and the rate of the slurry catalyst feed rate was adjusted to maintain a constant production rate of polymer. Additional catalyst is added as a liquid into the mineral oil suspension on the way into the polymerization reactor, and will anchor onto the catalyst particles and get activated by the MAO. This additional catalyst is called trim and is used to fine tune the molecular weight of the polymer that is being made. The additional catalyst is (tetramethylcyclopentadiene)(n-propylcyclopentadiene) zirconium dimethyl. The reacting bed of growing polymer particles was maintained in a fluidized state by the continuous flow of the make-up feed and recycle gas through the reaction zone. A superficial gas velocity of 0.6-0.9 meters/sec was used to achieve this.

A continuity additive was also injected directly into the reactor as a slurry in purified mineral oil at a concentration of 40 ppmw based on production rate. The following continuity additives were used in this example as indicated in the table below: a mixture of aluminum distearate and an ethoxylated amine type compound (IRGASTAT AS-990, available from Huntsman (formerly Ciba Specialty Chemicals), referred to in this example as CA-1; a second continuity additive referred to in this example as CA-2; and a third continuity additive referred to in this example as CA-3.

The fluidized bed was maintained at a constant height by withdrawing a portion of the bed at a rate equal to the rate of formation of particulate product. The rate of product formation (the polymer production rate) was in the range of 15-25 kg/hour. The product was removed semi-continuously via a series of valves into a fixed volume chamber. This product was purged to remove entrained hydrocarbons and treated with a small steam of humidified nitrogen to deactivate any trace quantities of residual catalyst.

Surprisingly, the polymerization data shown in the table below shows that the decreasing the temperature of the inlet gas in the spray-drying process resulted in productivity increases of up to 40% or even more in some instances, as shown in the table below.

TABLE 2

| Catalyst System Type | Spray-Drying Temp, ° C. | Continuity Additive | Productivity g/g | % Productivity Increase |
|---|---|---|---|---|
| A | 172 | CA-1 | 7416 | — |
| B | 140 | CA-1 | 11615 | 57% |
| A | 172 | CA-2 | 9006 | — |
| B | 140 | CA-2 | 12867 | 43% |
| A | 172 | CA-3 | 10117 | — |
| B | 140 | CA-3 | 12037 | 19% |
| B | 140 | CA-3 | 12057 | 19% |

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used. In the preceding description and the appended claims, the singular forms "a," "an" and "the" include plural referents unless otherwise specified.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited; in the same way, ranges from any upper limit may be combined with any other upper limit to recite a range not explicitly recited.

All documents and references cited herein, including testing procedures, publications, patents, journal articles, etc. are herein fully incorporated by reference for all jurisdictions in which such incorporation is permitted and to the extent such disclosure is consistent with the description of the present invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Although individual embodiments are discussed, the invention covers all combinations of all those embodiments.

What is claimed is:

1. A method for producing a catalyst system, comprising:
   providing a catalyst composition comprising a non-polar solvent and a single-site catalyst component, wherein the non-polar solvent comprises at least one hydrocarbon selected from the group consisting of toluene, benzene, hexane, and combinations thereof;
   heating an inert gas to a temperature that is from about 20% to about 35% greater than a boiling point of the non-polar solvent selected from the group consisting of toluene, benzene, hexane, and combinations thereof, based on the Centigrade scale; and
   spray drying the catalyst composition in the presence of the inert gas to form a spray-dried catalyst system comprising the single-site catalyst component, wherein the spray-dried catalyst system has an increase in productivity of at least about 10% in a polymerization reaction, as compared to another spray-dried catalyst system prepared from the same catalyst composition in a process that comprises heating the inert gas to a temperature of at least about 160° C.

2. The method according to claim 1, wherein the single-site catalyst component comprises a metallocene catalyst selected from the group consisting of a bis(n-propyl cyclopentadienyl)-$MX_2$, a (pentamethylcyclopentadienyl)(n-propylcyclopentadienyl)$MX_2$, a bis(indenyl)-$MX_2$, a (tetramethylcyclopentadienyl) (n-propyl cyclopentadienyl) $MX_2$, and any combination thereof, wherein M is zirconium, hafnium or titanium and X is methyl, chlorine, bromine, or fluorine.

3. The method according to claim 1, wherein the single-site catalyst comprises a Group 15-containing catalyst selected from the group consisting of [2,4,6-$Me_3C_6H_2$) $NCH_2CH_2]_2NH$ $MBz_2$ and [2,3,4,5,6-$Me_5C_6$)$NCH_2CH_2]_2$ NH $MBz_2$, wherein M is a Group 4 metal, each Bz is independently a benzyl group, and Me is methyl.

4. The method according to claim 1, wherein the single-site catalyst component comprises at least one catalyst selected from the group consisting of a metallocene catalyst, a Group 15-containing catalyst, and any combination thereof.

5. A polymerization process comprising combining an olefin with the spray-dried catalyst composition prepared by:
   providing a catalyst composition comprising a non-polar solvent and a single-site catalyst component, wherein the non-polar solvent comprises at least one hydrocarbon selected from the group consisting of toluene, benzene, hexane, and combinations thereof;
   heating an inert gas to a temperature that is from about 20% to about 35% greater than a boiling point of the non-polar solvent selected from the group consisting of toluene, benzene, hexane, and combinations thereof, based on the Centigrade scale; and
   spray drying the catalyst composition in the presence of the inert gas to form a spray-dried catalyst system comprising the single-site catalyst component, wherein the spray-dried catalyst system has an increase in productivity of at least about 10% in a polymerization reaction, as compared to another spray-dried catalyst system prepared from the same catalyst composition in a process that comprises heating the inert gas to a temperature of at least about 160° C.

6. The polymerization process according to claim 5, wherein the olefin comprises ethylene or propylene.

7. A method for producing a catalyst system, comprising:
   providing a catalyst composition comprising a non-polar solvent, an activator, a filler material, a metallocene catalyst, and a Group 15-containing catalyst, wherein the non-polar solvent comprises at least one hydrocarbon selected from the group consisting of toluene, benzene, hexane, and combinations thereof;
   heating an inert gas to a temperature that is from about 20% to about 35% greater than a boiling point of the non-polar solvent, based on the Centigrade scale; and
   spray drying the catalyst composition in the presence of the inert gas to form a spray-dried catalyst system comprising the activator, the filler material, the metallocene catalyst, and the Group 15-containing catalyst, wherein the spray-dried catalyst system has an increase in productivity of at least about 10% in a polymerization reaction, as compared to another spray-dried catalyst system prepared from the same catalyst composition in a process that comprises heating the inert gas to a temperature of at least about 160° C.

8. The method according claim 7, wherein the metallocene catalyst comprises a catalyst selected from the group consisting of a bis(n-propyl cyclopentadienyl)-MX$_2$, a (pentamethylcyclopentadienyl)(n-propylcyclopentadienyl)MX$_2$, a bis(indenyl)-MX$_2$, a (tetramethylcyclopentadienyl) (n-propyl cyclopentadienyl) MX$_2$, and any combination thereof wherein M is zirconium, hafnium or titanium and X is methyl, chlorine, bromine, or fluorine.

9. The method according to claim 7, wherein the Group 15-containing catalyst comprises a component selected from the group consisting of [2,4,6-Me$_3$C$_6$H$_2$)NCH$_2$CH$_2$]$_2$NH MBz$_2$ and [2,3,4,5,6-Me$_5$C$_6$)NCH$_2$CH$_2$]$_2$NH MBz$_2$, wherein M is a Group 4 metal, each Bz is independently a benzyl group, and Me is methyl.

10. The method according to claim 7, wherein the activator comprises an aluminoxane.

11. The method according to claim 7, wherein the filler material comprises fumed silica.

12. A polymerization process comprising combining an olefin with the spray-dried catalyst composition prepared according to claim 7.

13. The polymerization process according to claim 12, wherein the olefin comprises ethylene or propylene.

14. The polymerization process according to claim 12, wherein the polymerization process occurs in a gas phase reactor.

* * * * *